United States Patent [19]

Matsutani

[11] Patent Number: 4,722,384
[45] Date of Patent: Feb. 2, 1988

[54] METHOD OF AND APPARATUS FOR ATTACHING SUTURE TO OPERATING NEEDLE

[75] Inventor: Kanji Matsutani, Takanezawa, Japan

[73] Assignee: Matsutani Seisakusho Co., Ltd., Japan

[21] Appl. No.: 912,596

[22] Filed: Sep. 29, 1986

[51] Int. Cl.$^4$ .............................................. B41G 1/06
[52] U.S. Cl. ........................................ 163/1; 72/448; 163/5
[58] Field of Search ................... 29/568; 72/434, 416, 72/452, 448, 481; 83/411 R; 163/1-5

[56] References Cited

U.S. PATENT DOCUMENTS 4,306,443 12/1981 Matsutani .............................. 72/434
4,331,049 5/1982 Bergmann et al. ............ 83/411 R X
4,423,546 1/1984 Scott et al. .............................. 29/568

FOREIGN PATENT DOCUMENTS 33110 8/1953 Japan .

*Primary Examiner*—Mark Rosenbaum
*Attorney, Agent, or Firm*—Kane, Dalsimer, Kane, Sullivan & Kurucz

[57] ABSTRACT

A method of and an apparatus for staking a proximal end of an operating needle, with one end of a suture being inserted into a bore in the proximal end of the needle, to attach the suture to the needle. A staking unit has a pair of staking disc at least one of which is movable relative to the other. The dies are respecitvely provided therein with recesses between which the proximal end of the needle is staked. The staking unit is mounted on a table so as to be demountable therefrom. An electric power supply unit is provided which is separate from the staking unit, but is connected thereto through a plug and a socket. A foot switch is connected to the power supply unit for controlling the operation of the staking unit. A plurality of the staking units are prepared which include their respective pairs of staking dies different in dimension of the recesses from each other. One of the staking units is selected, which includes its corresponding pair of staking dies adapted to a needle to be staked.

12 Claims, 7 Drawing Figures

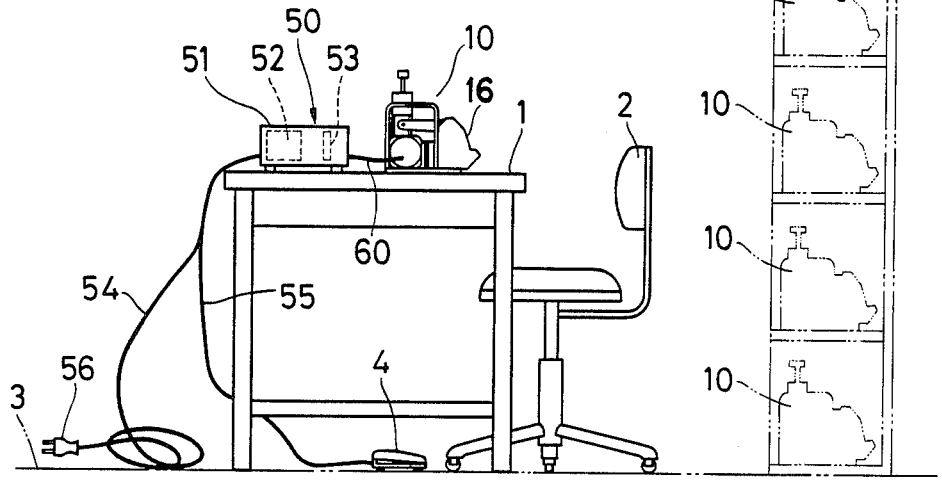
Fig. 1
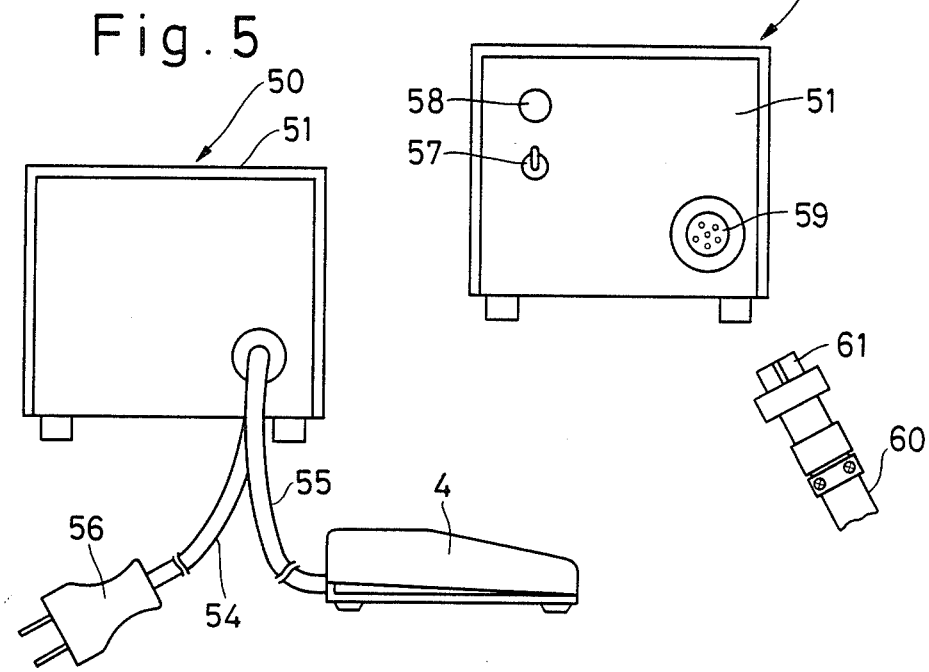
Fig. 5
Fig. 6

METHOD OF AND APPARATUS FOR ATTACHING SUTURE TO OPERATING NEEDLE

BACKGROUND OF THE INVENTION

The present invention relates to a method of and apparatus for attaching a suture to an operating needle.

Various apparatus of the kind referred to above are known in which one end of a suture is inserted into a bore formed in a proximal end of an operating needle and extending along an axis thereof, and the end of the operating needle is clamped between recesses respectively formed in forward ends of respective movable and fixed staking dies and is staked thereby, to attach the suture to the operating needle. The fixed staking die is supported on a staking base in immovable relation thereto, and the movable staking die is also supported on the staking base for movement toward and away from the fixed staking die. The known apparatuses are divided broadly into three types.

First one of the above three types is an apparatus which utilizes human power. Specifically, the apparatus is arranged such that a foot pedal is operated to move the movable staking die toward the fixed staking die through a linkage. The second type of apparatus is arranged such that a foot pedal or a foot switch is operated to actuate a hydraulic cylinder, to thereby cause the force from the hydraulic cylinder to move the movable staking die toward the fixed staking die. The third type of apparatus is one developed by the inventor of the present application, in which the movable staking die is moved by a motor. Typical apparatus of such third type is disclosed in U.S. Pat. No. 4,306,443 issued to Matsutani on Dec. 22, 1981. In all of the apparatuses of the types referred to above, the staking base is fixedly mounted on a table.

There are many kinds of operating needles, and the proximal ends of the respective needs are various in outer diameter, for example. In order to perform an optimum staking, it is necessary to change the radii of the recesses in the respective movable and fixed staking dies, depending upon the outer diameters of the proximal ends of the needles.

In all of the apparatuses of the types described above, the staking base is fixed to the table and, accordingly, if it is desired to stake a different kind of needles, it is required to remove the fixed and movable staking dies from the staking base, and to substitute therefor another fixed and movable staking dies. Such substituting or replacing operation, however, is very troublesome.

In addition, if circumstances require, it is necessary to change or vary the staking force in accordance with the outer diameters of the proximal ends of the needles and the diameters of the sutures. However, the staking force has to be re-adjusted each time the types of the needle to be staked are changed. This is troublesome and requires considerable skill.

Thus, the known apparatuses cannot be said to be suitable for a multiple-kind and small-quantity production.

OBJECT AND SUMMARY OF THE INVENTION

An object of the present invention is to provide a method of and an apparatus for attaching a suture to an operating needle, which improve the above-described third type of apparatus to enhance the productivity in a multiple-kind and small-quantity production.

According to the invention, there is provided a method of staking a proximal end of an operating needle, with one end of a suture being inserted into a bore formed in the proximal end of the needle and extending along an axis thereof, to attach the suture to the needle, the method comprising the steps of:

preparing a single electric power supply unit and a single foot switch connected to the electric power supply unit;

preparing a plurality of staking units each comprising a staking base, a pair of staking dies supported on the staking base, at least one of the pair of staking dies being movable relative to the other toward and away from latter, each of the pair of staking dies having a forward end thereof provided therein with a recess, a motor mounted on the staking base, and a power transmitting mechanism for transmitting rotation of the motor to the at least one die to move the same toward the other staking die so as to stake the proximal end of the needle between the respective recesses in the pair of staking dies, the pairs of staking dies of the respective staking units being different in dimension of the recesses from each other;

selecting one of the plurality of staking units, which includes its corresponding pair of staking dies adapted to an operating needle to be staked;

connecting the selected staking unit to the electric power supply unit through a connector; and operating the foot switch to permit electric current to be supplied from the electric power supply unit to the motor of the selected staking unit, to thereby perform the staking.

According to the invention, there is further provided an apparatus for staking a proximal end of an operating needle, with one end of a suture being inserted into a bore formed in the proximal end of the needle and extending along an axis thereof, to attach the suture to the needle, the apparatus comprising:

a staking unit mounted on a table so as to be demountable therefrom and including a staking base, a pair of staking dies supported on the staking base, at least one of the pair of staking dies being movable relative to the other toward and away from the latter, each of the pair of staking dies having a forward end thereof provided therein with a recess, a motor mounted on the staking base, and a power transmitting mechanism for transmitting rotation of the motor to the at least one die to move the same toward the other staking die so as to stake the proximal end of the needle between the respective recesses in the pair of staking dies;

an electric power supply unit;

cord means and connector means through which the electric power supply unit is connectable to the motor of the staking unit; and a foot switch electrically connected to the electric power supply unit and operable to supply an ON signal thereto to permit electric current to flow from the electric power supply unit to the motor to render the same operative.

BRIEF DESCRIPTION OF THE DRAWINGS

FIG. 1 is a schematic side elevational view showing an embodiment of an apparatus for attaching a suture to an operating needle, in accordance with the invention;

FIG. 5 is a rear view showing an electric power supply unit illustrated in FIG. 1;

FIG. 6 is a front elevational view showing the electric power supply unit illustrated in FIG. 1.

DETAILED DESCRIPTION

Figure 2:
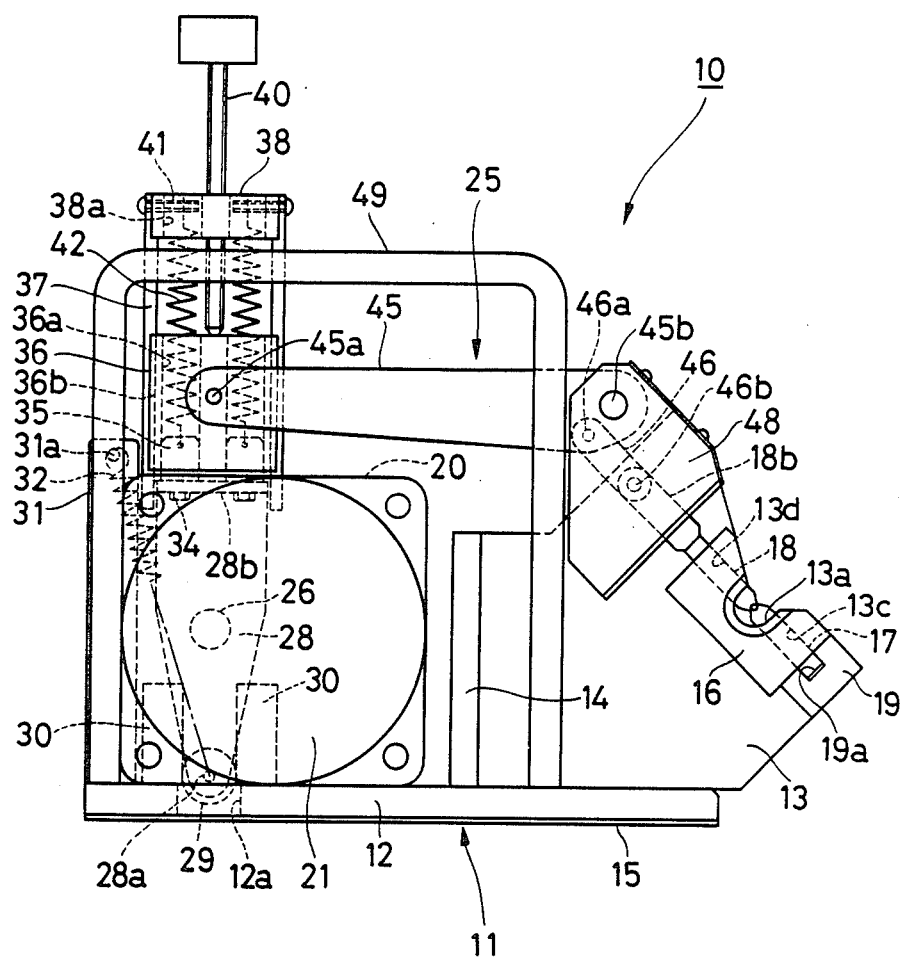
FIG. 2 is an enlarged side elevational view showing a staking unit illustrated in FIG. 1.

An embodiment of the invention will now be described with reference to the drawings.

Referring to FIG. 1, an apparatus for attaching a suture to an operating needle comprises a staking unit 10 and an electric power supply unit 50 which are mounted on a top surface of a work table 1 so as to be demountable therefrom. A chair 2 is arranged in front of the table 1. A foot switch 4 is arranged on a floor 3 on which the table 2 rests.

As shown in detail in FIG. 2, the staking unit 10 includes a staking base 11 which is comprised of a horizontal plate 12, a vertical plate 13 fixedly secured to an upper surface of a front part (right part in the figure) of the horizontal plate 12, and a vertical plate 14 fixedly secured to the upper surface of the horizontal plate 12 and having a front surface fixedly connected to a rear end of the vertical plate 13. The horizontal plate 12 has a lower surface thereof to which a rubber sheet 15 is adhesively bonded to prevent the staking base 11 from slipping relative to the table 1.

Figure 3:
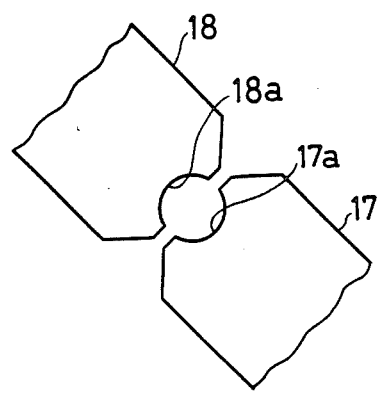
FIG. 3 is a fragmentary side elevational a view illustrating, in an enlarged scale, forward ends of respective fixed and movable staking dies illustrated in FIG. 2.

The vertical plate 13 has an inclined surface in which a working recess 13a is formed. A pair of aligned grooves 13c and 13d are formed in one side surface of the vertical plate 13, and obliquely extend from the opposite sides of the recess 13a. A fixed staking die 17 is received in the groove 13c, and a movable staking die 18 is received in the groove 13d. The fixed staking die 17 has a proximal end thereof which is inserted into and engaged with a recess 19a in a support block 19 fixedly secured to the side surface of the vertical plate 13, and the proximal end of the fixed staking die 17 is fixed to the support block 19 by means of a screw or bolt, not shown. The movable staking die 18 is supported in the recess 13d for sliding movement therealong toward and away from the fixed staking die 17. Forward ends of the respective fixed and movable staking dies 17 and 18 face the working recess 13a, and have semicircular recesses 17a and 18a, respectively, as shown in FIG. 3. Referring back to FIG. 2, a cover 16 is fixedly secured to the side surface of the vertical plate 13 so as to cover the fixed and movable staking dies 17 and 18.

A gear box 20 having a reduction gear train housed therein is fixedly mounted on the upper surface of the horizontal plate 12 of the staking base 11 by means of angled members or the like, not shown. The gear box 20 has a side surface thereof to which a motor 21 is fixedly mounted. The motor 21 has an output shaft connected to the reduction gear train. Rotation of the motor 21 is converted to the movement of the movable staking die 18 by means of a power transmitting mechanism 25 which includes the aforesaid reduction gear train.

Figure 4:
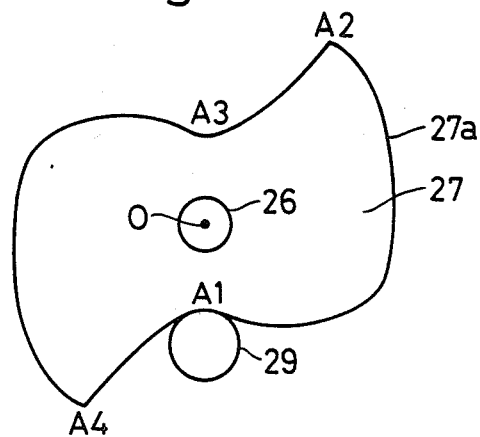
FIG. 4 is an enlarged side elevational view showing a cam disc and a roller incorporated into the staking unit illustrated in FIG. 2.

The fundamental construction of the power transmitting mechanism 25 is known from U.S. Pat. No. 4,306,443 referred to previously. However, the power transmitting mechanism 25 illustrated herein has slight improvements added to that disclosed in the U.S. patent. More specifically, the reduction gear train has an output shaft 26 on which a cam disc 27 is mounted for rotation therewith. The cam disc 27 is omitted from FIG. 1 for simplification, but is shown in FIG. 4. The cam disc 27 has a cam surface 27a formed on an outer periphery thereof, and a roller 29 is disposed to abut against the lower running side of the cam surface 27a. The roller 29 is rotatably supported on a lower end of a cam follower 28 through a pin 28a. The roller 29 is restrained in its lateral movement or shift, but is allowed only to be moved up and down by a pair of upstanding guides 30 and 30 which are fixedly secured to the upper surface of the horizontal plate 12. A bore 12a is formed in the horizontal plate 12 to permit the roller 29 to be moved into and out of the bore 12a. A pole 31 is fixedly secured to the upper surface of the horizontal plate 12 at a location adjacent one of the upstanding guides 30. A coil spring 32 is connected under tension between a pin 31a on an upper end of the pole 31 and the pin 28a on the cam follower 28, to always bias the cam follower 28 upwardly, so that the roller 29 is always brought into abutment against the cam surface 27a.

Another cam disc, not shown, is mounted on the output shaft 26 for rotation therewith. A limit switch, not shown, for controlling the motor 21 is disposed adjacent the another cam disc. When rotated, the another cam disc actuated the limit switch between its ON and OFF positions.

The cam follower 28 is comprised of an elongated plate, and a flange 28b is provided at an upper end of the cam follower 28. Two sliders 35 are fixedly mounted on the flange 28b by means of bolts 34, and are slidably received respectively in vertically extending bores 36a formed in a movable block 36.

The movable block 36 has its opposite side surfaces in each of which a vertically extending groove 36b is formed. Each of two elongated sliders 37 is slidably received in a corresponding one of the grooves 36b. An adjusting block 38 is fixedly secured to the upper ends of the respective sliders 37. An adjusting screw 40 is threadedly engaged with a threaded bore formed at a central portion of the adjusting block 38. In addition, the adjusting block 38 is formed therein with two vertical bores 38a, and two screws 41 are screwed into the adjusting block 38 so as to extend respectively across the vertical bores 38a. Each of two coil springs 42 having a relatively high resiliency is connected under tension between a corresponding one of the screws 41 and a correspsonding one of the sliders 35. By the two coil springs 42, the adjusting block 38 and the sliders 37 are biased downwardly to always bring the lower end of the adjusting screw 40 into abutment against the upper surface of the movable block 36. Thus, the movable block 36 is also biased toward the cam follower 28 by the resilient force of the coil springs 42. Except for a staking position shown in FIG. 2, the movable block 36 normally abuts against the flange 28b of the cam follower 28.

An arm 45 has one end thereof pivotally connected to the movable block 36 through a pin 45a, and the other end pivotally connected to the upper end of the aforesaid vertical plate 13 through a pin 45b. A link 46 has one end thereof pivotally connected to the other end of the arm 45 through a pin 46a, and the other end pivotally connected, through a pin 46b, to an end of an extension 18b of the aforementioned movable staking die 18.

A cover 48 is fixedly secured to the upper portion of the side surface of the vertical plate 13 so as to cover the link 46 and the like. A grip 49 in the form of an inverted letter U has a pair of legs having their respective lower ends fixedly secured to the upper surface of the horizontal plate 12, so that an operator can hold the grip 49 to carry the staking unit 10 to and from any desired location.

The above-described electric power supply unit 50 comprises, as shown in FIG. 1, a housing 51, transformer 52 arranged within the housing 51, and a control circuit 53 arranged within the housing 51 and electrically connected to the transformer 52. As shown in FIGS. 1 and 5, a first cord 54 and a second cord 55 extend from a rear surface of the housing 51. The first cord 54 has one end thereof connected to the transformer 52 within the housing 51, and the other end connected to a plug 56 which is connectable to a plug socket or receptacle (not shown) on the side of an electric power source. The second cord 55 has one end thereof connected to the control circuit 53 within the housing 51, and the other end connected to the foot switch 4. As shown in FIG. 6, the housing 51 has a front surface provided thereon wih a switch 57 for switching on and off the connection between the electric power source and the transformer 52, and a pilot lamp 58 indicating the ON and OFF conditions. The front surface of the housing 51 is also provided thereon with a receptacle 59 which is connected to the control circuit 53 within the housing 51. A cord 60 extending from the staking unit 10 has a forward end provided thereat with a plug 61 which is detachably connectable to the receptacle 59. The cord 60 includes a leading wire connected to the motor 21 and a leading wire connected to the aforesaid limit switch for controlling the motor 21.

When it is desired for the apparatus constructed as described above to carry out a multiple-kind and small-quantity production, a plurality of staking units 10 having mounted thereon their respective pairs of fixed and movable staking dies 17 and 18 different in radii of the recesses 17a and 18a from each other are prepared for a single table 1, single power supply unit 50 and a single foot switch 4. One of the staking units 10, which includes its corresponding pair of staking dies 17 and 18 adapted to an operating needle to be staked, is selected and mounted on the table 1, and the plug 61 of the cord 60 is connected to the receptacle 59 of the power supply unit 50 in the manner described previously. The remaining staking units 10 are stored within a storage rack 70 adjacent the table 1.

The operation of attaching a suture to an operating needle will now be described. When the motor 21 is rendered inoperative, the cam disc 27 occupies its angular position shown in FIG. 4, and the roller 29 on the cam follower 28 is brought into contact with a location A1 of the cam surface 27a. The location A1 is closest in distance to the center of rotation 0 of the cam disc 27 and, accordingly, the cam follower 28 is located at the uppermost position. Under such condition, the movable staking die 18 is located at a position farthest from the fixed staking die 17.

Figure 7:
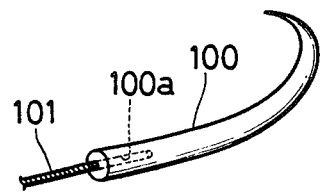
FIG. 7 is an enlarged perspective view showing an opertating needle to which a suture is attached.

As shown in FIG. 7, one end of a suture 101 is inserted into a bore 100a which is formed in a proximal end of an operating needle 100 and extends along an axis thereof. The proximal end of the needle 100 is then fitted and set in the recess 17a in the fixed staking die 17.

Subsequently, as the foot switch is depressed by a foot of an operator, an ON signal is supplied from the foot switch 4 to the control circuit 53, so that the electric current is permitted to flow from the transformer 52 of the electric power supply unit 50 to the motor 21 to render the same operative. Then, the output shaft 26 of the reduction gear train is rotated to rotate the cam disc 27 in the clockwise direction as viewed in FIG. 4, and the contacting position of the cam surface 27a with the roller 29 is moved from the position A1 toward a position A2. This gradually increases the distance between the contacting position and the center of rotation 0 and, correspondingly, the cam follower 28 is moved downwardly to tend to stretch the coil springs 42. Then, the resilient force of the coil springs 42 causes the movable block 36 to follow the cam follower 28 and to be moved downwardly, to thereby cause the arm 25 to be angularly moved about the pin 45b in the counterclockwise direction in FIG. 2. As a result, the movable staking die 18 is moved toward the fixed staking die 17.

Before the roller 29 reaches the position A2 of the cam surface 27a, the recess 18a in the movable staking die 18 impinges against the proximal end of the needle 100. Subsequently, the staking operation is started to deform the proximal end of the needle 100 under the resilient force of the coil springs 42. The resilient force of the coil springs 42 is amplified on the principles of lever due to the arm 45, and is transmitted to the movable staking die 18 through the link 46. As the deformation of the proximal end of the needle 100 proceeds to a certain extent, the proximal end of the needle 100 is no longer deformed under the resilient force of the coil springs 42. Thus, the angular movement of the arm 45 about the pin 45b stops, and the downward movement of the movable block 36 stops. Subsequently, the cam follower 28 is singly moved downwardly, and the flange 28b of the cam follower 28 is moved away from the movable block 36.

As the cam disc 27 continues to be rotated to move the contacting position of the cam surface 27a with the roller 29 from the position A2 toward a position A3, the cam follower 28 is in turn moved upwardly and, correspondingly, the movable block 36 is moved upwardly directed by the upward movement of the cam follower 28 to allow the movable staking die 18 to be move away from the fixed staking die 17. As the contacting position of the cam surface 27a with the roller 29 reaches the position A3, the limit switch is actuated to supply the OFF signal to the control circuit 53, to thereby render the motor 21 inoperative.

Subsequently, the needle 100 is turned through 90 degrees about its own axis, and is again set in the recess 17a in the fixed staking die 17. The foot switch 4 is again depressed to re-sart the staking operation similar to that described above. In the course of this staking operation, the contacting position of the cam surface 27a with the roller 29 is moved with the position A3 to the position A1 through a position A4.

In the manner as described above, the staking operation is completed, and the suture 101 is attached to the needle 100. The staking force is determined depending upon the resilient force of the coil springs 42 which can be adjusted in such a manner that the adjusting screw 40 is turned to vary the distance between the adjusting block 38 and the movable block 36, to thereby adjust the length of the coil springs 42.

When it is desired to perform the staking operation with respect to another needle 100 having a different outer diameter, another staking unit 10 having mounted thereon fixed and movable staking dies 17 and 18 having their respective recesses 17a and 18a adapted to the another needle 100 is taken out of the storage rack 70 and is substituted for the previously used staking unit. At this time, it is sufficient if the plug 61 is merely disconnected from the receptacle 59 of the previously used staking unit and is connected to the receptacle 59 of the another staking unit. Thus it is made possible to facilitate the substituting or replacing operation. Subsequently, the another staking unit 10 is employed to again perform the staking operation with respect to the another needle.

The above-noted staking force is previously adjusted for each of the staking units 10 so as to obtain its corresponding optimum staking force. Accordingly, it is not required to adjust the staking force each time needles 100 to be staked change in kind or type. This also makes it possible to enhance the operability or workability.

As described above, it is not required to replaced the fixed and movable staking dies 17 and 18 and to adjust the staking force each time needles to be staked change in kind or type. This enables the staking operation to be re-started quickly. Thus, it is made possible to enhance the productivity in a multiple-kind and small-quantity production. In addition, it is advantageous that skill is not so much requested for as operator who practically performs the staking operation.

The invention should not be limited to the specific embodiment described above, but various changes and modifications may be made. For example, in place of the extension 18b of the movable staking die 18, a rod independent thereof may be used in such a manner that a pre-loading mechanism is provided at an end of the rod adjacent the movable staking die 18, as disclosed in U.S. Pat. No. 4,306,443 referred to above. The pre-loading mechanism comprises a spring and a pin biased by the spring so as to be urged against the movable staking die. In this case, it is possible to hold a needle between the fixed and movable staking dies by the resiliency of the spring before staking. It is to be noted, in this case, that the movable staking die is required to be always biased toward the rod by means of a return spring which is weaker in resiliency than the spring of the pre-loading mechanism.

Furthermore, a pair of positioning plates, as disclosed in Japanese Utility Model Application Laid-Open No. 55-33110 laid open to public inspection on Mar. 3, 1980, may be arranged respectively on the opposite sides of fixed and movable staking dies. The positioning plates are adjustable in their respective positions, in accordance with the diameter of the needle and the diameter of the suture. The adjustment of the positions is previously made for each of all the staking units, similarly to the aforesaid adjustment of the staking force, to eliminate the adjustment for each change in kind or type of needles.

Moreover, although the invention has been described as having a pair of staking dies, one being movable and the other being fixed, it should be appreciated by one skilled in the art that both staking dies may be movable toward and away from each other. In sum, it is sufficient if at least one of the pair of staking dies is movable relative to the other toward and away from the latter.

What is claimed is:

1. A staking apparatus for various types of operating needles, comprising:
   an electric power supply unit;
   a plurality of staking units each including a staking base, a motor mounted on said staking base, a connector connected to said motor and connectable to said electric power supply unit, a pair of staking dies supported on said staking base and each having a forward end formed therein with a recess and a power transmitting mechanism for transmitting rotation of said motor to at least one of said pair of staking dies to move said at least one of said staking dies toward the other staking die for applying a staking force to a proximal end of an operating needle located between the recesses of the respective staking dies, to thereby stake the proximal end of the operating needle to attach an end of a suture thereto, said power transmitting mechanism having incorporated therein adjusting means for adjusting said staking force, the pairs of staking dies of the respective staking units being different in recess dimension from pair to pair; and
   a foot switch electrically connected to said electric power supply unit,
   wherein selected one of said staking units is mounted on a work table so as to be detachable therefrom, said selected staking unit having an adjusted staking force individually preselected for each of said operating needles to be staked and having its corresponding pair of staking dies conformed in recess dimension to the type of operating needles to be staked, the connector of the selected staking unit is connected to said electric power supply unit, and said foot switch is operated to permit electric current to be supplied to the motor of the selected staking unit, to thereby perform the staking.

2. An apparatus as defined in claim 1, wherein at least one out of said pair of staking dies of each of said staking units is supported on the corresponding staking base for sliding movement relative thereto, and the other staking die is supported on the staking base in immovable relation thereto.

3. An apparatus as defined in claim 1, including:
   a first and a second cord extending from said electric power supply unit, said first cord having a forward end thereof connected to said foot switch;
   a connector provided at a forward end of said second cord and connectable to an electric power source;
   a connector provided on a housing of said electric power supply unit; and
   the connector means of each of said staking units being connectable to said connector provided on said housing of said electric power supply unit.

4. An apparatus as defined in claim 1, wherein said electric power supply unit includes a transformer.

5. An apparatus as defined in claim 1, wherein said electric power supply unit further includes a control circuit connected to said transformer.

6. An apparatus as defined in claim 1, wherein each of said staking units includes a grip fixedly mounted on the corresponding staking base for permitting an operator to hold said grip to carry the staking unit to and from any desired location.

7. An apparatus as defined in claim 1, wherein the staking base of each said staking units includes a horizontal plate, the corresponding motor being mounted on said horizontal plate, a vertical plate fixedly mounted on said horizontal plate, and an inverted U-shaped grip having a pair of legs having their respective lower ends fixedly secured to said horizontal plate, the corresponding pair of staking dies being supported on said vertical plate.

8. An apparatus as defined in claim 7, wherein the staking base of each of said staking units further includes a rubber sheet secured to a lower surface of the corresponding horizontal plate for preventing the staking base from slipping relative to said table.

9. An apparatus as defined in claim 1, wherein said power transmitting mechanism of each of said staking units includes;
cam means having a cam surface and drivingly connected to the corresponding motor so as to be rotated thereby;
cam follower means disposed to abut against said cam surface of said cam means and movable thereby in a first direction and a second direction opposite thereto when said cam means is rotated by the motor;
spring means having one end thereof connected to said cam follower means;
movable block means associated with the other end of said spring means and movable in a first direction and a second direction opposite thereto, the movement of said cam follower means in its first direction causing said spring means to tend to be stretched and the resilient force of said spring means causing said movable block means to be moved in its first direction, and said movable block means being moved in its second direction by the movement of said cam follower means in its second direction;
linkage means connected between said movable block means and the a least one staking die, the movement of said movable block means in its first direction being transmitted to the at least one staking die through said linkage means to move the at least one staking die toward the other staking die, and the movement of said movable block means in its second direction being transmitted to the at least one staking die through said linkage means to move the at least one staking die away from the other staking die, and
the corresponding adjustment means being arranged to adjust the resilient force of said spring means.

10. A new method of using a staking apparatus for various types of operating needles, said staking apparatus comprising a single electric power supply unit, a single foot switch connected to said electric power supply unit, and a plurality of staking units each including a base, a motor mounted on said base, a connector connected to said motor and connectable to said electric power supply unit, a pair of staking dies supported on said base and each having a forward end formed therein with a recess, and a power transmitting mechanism for transmitting rotation of said motor to at least one of said pair of staking dies to move said at least one staking die toward the other staking die for applying a staking force to a proximal end of an operating needle located between the recesses of the respective staking dies, to thereby stake the proximal end of the operating needle to attach an end of a suture thereto, said power transmitting mechanism having incorporated therein adjusting means for adjusting said staking force, the pairs of staking dies having different recess dimensions from pair to pair, said method comprising the steps of:
operating the adjusting means of the staking units for adjusting the staking forces to individually preselected values for each of said operating needles to be staked;
selecting one said staking units, which has an adjusted staking force individually preselected for each of said operating needles to be staked and which has its corresponding pair of staking dies conformed in recess dimension to the type of operating needles to be staked;
connecting the connector of the selected staking unit to said electric power supply unit; and
operating said foot switch to permit electric current to be supplied to the motor of the selected staking unit, to thereby perform the staking.

11. A method as defined in claim 10, wherein at least one out of said pair of staking dies of each of said staking units is supported on corresponding staking base for sliding movement relative thereto, and the other staking die is supported on the staking base in immovable relation thereto.

12. A method as defined in claim 10, including the step of:
storing the remaining staking units in a storage rack arranged adjacent a table on which said selected staking unit is mounted.

* * * * *